United States Patent
Tom-Moy et al.

(10) Patent No.: US 6,586,232 B2
(45) Date of Patent: *Jul. 1, 2003

(54) SUBSTRATE PREPARATION FOR CHEMICAL-SPECIES-SPECIFIC BINDING

(75) Inventors: May Tom-Moy, San Carlos, CA (US); Carl Alan Myerholtz, Cupertino, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/814,360

(22) Filed: Mar. 21, 2001

(65) Prior Publication Data

US 2002/0192718 A1 Dec. 19, 2002

Related U.S. Application Data

(60) Division of application No. 07/876,804, filed on Apr. 29, 1992, now Pat. No. 6,235,488, which is a continuation of application No. 07/404,721, filed on Sep. 8, 1989, now abandoned, which is a continuation-in-part of application No. 07/251,149, filed on Sep. 29, 1988, now Pat. No. 5,130,257.

(51) Int. Cl.$^7$ .............. C12Q 1/68; C12M 1/34; C12P 1/68; C07H 21/02; G01N 33/543

(52) U.S. Cl. ............ 435/285.2; 435/6; 435/7.1; 435/7.5; 435/91.1; 435/91.2; 435/287.2; 536/22.1; 536/23.1; 536/24.3; 536/24.31; 536/24.32; 536/24.33; 436/517; 436/518; 436/536

(58) Field of Search ............... 435/6, 7.1, 7.5, 435/91.1, 91.2, 285.2, 287.2; 436/517, 518, 536

(56) References Cited

U.S. PATENT DOCUMENTS 4,916,055 A * 4/1990 Yeoman et al. ............... 435/7

* cited by examiner

Primary Examiner—Jeffrey Siew

(57) ABSTRACT

A mass biosensor uses an intermediate avidin layer to facilitate binding of a biotinylated antibody to a measurement surface of the biosensor. The avidin layer can be added by the manufacturer of the biosensor, while the biotinylated layer can be added by the user. This two-phase method of chemically modifying the measurement surface significantly reduces the user time required to customize the measurement surface to render it capable of binding selected compounds. An organosilane coupling agent attached to the surface provides sites to which avidin is bound. Avidin acts as a universal receptor of biotinylated compounds with specific binding affinities. Biotinylated antibodies or other biotinylated compounds are added and bind to the immobilized avidin. Surface adsorption is reduced by washing the modified surface with biotin to block potential sites of weak bond formation, electrostatic and hydrophobic interactions.

3 Claims, 3 Drawing Sheets

SUBSTRATE PREPARATION FOR CHEMICAL-SPECIES-SPECIFIC BINDING

REFERENCE TO PRIOR APPLICATIONS

This is a divisional application of application Ser. No. 07/876,804 filed on Apr. 29, 1992, now U.S. Pat. No. 6,235,488, which is a continuation of application Ser. No. 07/404,721 filed on Sep. 8, 1989, now abandoned, which is a continuation-in-part of Ser. No. 07/251,149 filed on Sep. 29, 1988, now U.S. Pat. No. 5,130,257; each of these prior applications is hereby incorporated by reference.

BACKGROUND OF THE INVENTION

The present invention relates to analytical chemistry and, more particularly, to devices and methods which provide for selectively binding chemical species to a substrate. A major objective of the present invention is to provide for more convenient and effective chemical binding to a substrate used in the context of a mass biosensor.

Preservation of the environment requires that the amounts of various pollutants on land and in water be monitored. Laboratories monitoring these pollutants are charged with measuring microquantities of many different chemicals. Mass biosensors provide a valuable tool in this application, as well as in medical and other applications.

Mass biosensors are used to measure microquantities of biological components and have the potential for detecting trace amounts of biological and chemical components. One type of mass biosensor uses a piezoelectric crystal as an acoustic waveguide. An input transducer generates a periodic acoustic wave from a periodic electrical input signal. The acoustic wave propagates through the crystal to an output transducer which converts the received acoustic wave to an electrical output signal. The acoustic wave undergoes a change in propagation velocity which corresponds to the mass bound to the surface of the crystal. By monitoring the frequency or relative phases of the input and output electrical signals, the mass changes at the surface of the crystal can be measured.

To measure the amount of a specific chemical component in a sample solution, the surface of the crystal must be prepared to bind that component selectively. In one approach, a scientist obtains an unmodified crystal and prepares it shortly before component measurement so that it acquires an affinity for the component of interest. For example, an antibody can be bound to a crystal surface to prepare the mass biosensor to measure the amount of the corresponding antigen.

Heretofore, piezoelectric crystal biosensors were constructed so that antibody proteins which bind antigens or antibody-binding proteins which bind antibodies were bound directly to the surface. A major drawback of this method is the extensive amount of time necessary to bind these proteins to the surface, a procedure taking many hours. In some cases, the preparation procedures take 24 hours or more.

Another drawback is that the shelf life of the sensors is limited by the stability of the proteins bound on its crystal surface. Antibodies and antibody-binding proteins require cold storage and lose binding activity with time. Still another drawback is that some of the proteins can be attached to the surface in an orientation that obscures binding sites for the compound of interest. Additionally, the procedure for immobilizing the proteins on the surface exposes them to chemicals which can lower binding activity by affecting functional groups at the binding sites. Furthermore, the procedure can require additional modifications for each specific protein system. Yet another problem is the high degree of nonspecific adsorption on the surface: many molecules in solution will bind to the surface by means of weak electrostatic and hydrogen bonds. In a mass biosensor, this nonspecific binding affects the measurement, limiting the sensitivity of the instrument and its analytical and clinical usefulness.

What is needed is a quick and convenient procedure for customizing a sensor to bind chemicals of interest for diverse applications. Additionally needed is a sensor with minimal nonspecific binding so that it can be used in detecting trace quantities of chemicals of interest.

SUMMARY OF THE INVENTION

In accordance with the present invention, a measuring device includes a measurement surface, a ligand-binding layer on the surface, and a ligand-bearing layer bound to the ligand-binding layer. The ligand-bearing layer is selected for its binding affinity to a chemical to be measured. For example, a layer of a selected biotinylated antibody can be bound to an avidin layer, in turn bound to the piezoelectric crystal substrate of a mass biosensor.

Preparation of the measuring device involves chemically modifying the binding properties of the measurement surface by utilizing a ligand-conjugated compound having binding affinity for a chemical of interest and also utilizing a substance having reciprocal ligand-binding sites. The preparation steps comprise attaching the ligand-binding substance as a layer to the surface, binding the ligand-bearing compound as a layer to the ligand-binding substance, and washing the resultant structure with a blocking agent which covers free active sites in order to reduce non-specific adsorption. The resulting composite surface can be used for selective binding of the chemical of interest. As an example, avidin can be coupled to a silica substrate, a biotinylated antibody can be attached to the avidin, and biotin can be added to block unoccupied active sites. This composite surface will bind tightly to antigen with minimal nonspecific adsorption.

As indicated, avidin is a favored material for the ligand-binding layer and biotinylated antibodies are appropriate for the ligand-bearing layer. A biotinylated antibody is composed of an antibody bound to biotin directly or via a spacer molecule. Biotin has one avidin-binding site per molecule and avidin has four biotin-binding sites per molecule. Avidin and biotin bind tightly to one another through their reciprocal binding sites, even when each is in turn conjugated to other molecules, as long as the high affinity binding sites are not blocked.

The present invention provides a device which, when immersed in a liquid, binds selected chemicals. The surface of the device has overlaying layers composed of ligand-binding substance and ligand-conjugated compound, the latter having strong binding affinity toward the chemicals of interest. The ligand-binding substance can be bound to the substrate using a coupling agent. Nonspecific binding can be controlled by pretreatment with blocking agents, buffers, or other regimen. Blocking agents are chemicals that bind to the device and sterically inhibit the nonspecific binding from weak bond formation. Buffers of appropriate pH can inhibit nonspecific binding by neutralizing charged sites on the surface.

A mass biosensor provided by the present invention includes an electric signal generator, an electro-acoustic input transducer, a piezoelectric crystal waveguide, an electro-acoustic output transducer, and means for measuring phase changes between the electric signals from the generator and output transducer. In this case, the waveguide is immersed in a liquid, a signal is applied, and the phase or frequency of the output signal from the waveguide is monitored. Mass changes on the surface of the waveguide affect the output signal and the mass or concentration of the analyte can be calculated from these data.

The present invention provides for preparation of the measurement surface in two phases to obviate problems of excessive preparation time and product instability. In accordance with the preferred embodiment, the first phase of preparation involves attaching avidin to the sensor surface. This phase, which is time consuming, can be accomplished efficiently by a manufacturer of the device. Avidin retains its binding activity at room temperature so that the avidin-coated device has a relatively long shelf life and, for manufacturing purposes, can be packaged and distributed without cold storage at considerable cost saving. A further advantage to the manufacturer is that avidin, which is a constituent of egg whites, can be abundantly supplied at low cost. Still another advantage for applications requiring sterile conditions is that the avidin-modified sensor can be sterilized since avidin withstands temperatures up to 120° C.

The second phase involves attaching a biotinylated compound to the avidin and blocking weak binding sites on the surface. This phase can be accomplished with ease by the user in about 30 minutes. Although biotinylated antibody is less stable than avidin, this component need not be added to the surface until just prior to use. Another advantage to the user is that the second phase of preparation requires no expensive apparatus or chemicals. Further, this phase of the procedure is accomplished at room temperature under physiological conditions so that the binding activity of the biotinylated compounds is not compromised by harsh chemicals or high temperatures. Of great convenience to the user is the fact that biotinylated compounds are available commercially or can be prepared following published procedures. Thus, the present invention significantly enhances the convenience with which mass biosensors can be customized to assess the amounts of selected chemicals.

An important feature of the present invention is that it can reduce nonspecific binding. Free, active binding regions on the silica surface are sterically blocked by bound avidin. Free, unbound sites on avidin are blocked in the final wash step with biotin. Since biotin is small and of low molecular weight, it has access to unbound binding sites that may otherwise be inaccessible to larger blocking agents because of steric hindrance.

Yet another feature of the invention is the multiplication of binding sites. Since a single molecule of avidin has four biotin binding sites, when a silica surface is overlaid with avidin, the number of potential binding sites for biotinylated derivatives is fourfold the number of binding sites for avidin. When using biotinylated antibodies for the next layer, each of which contains two antigen binding sites, potential binding sites for the antigenic species are amplified again. These and other features and advantages of the present invention will be apparent from the description below with reference to the following drawings.

DESCRIPTION OF THE PREFERRED EMBODIMENTS

Figure 1:
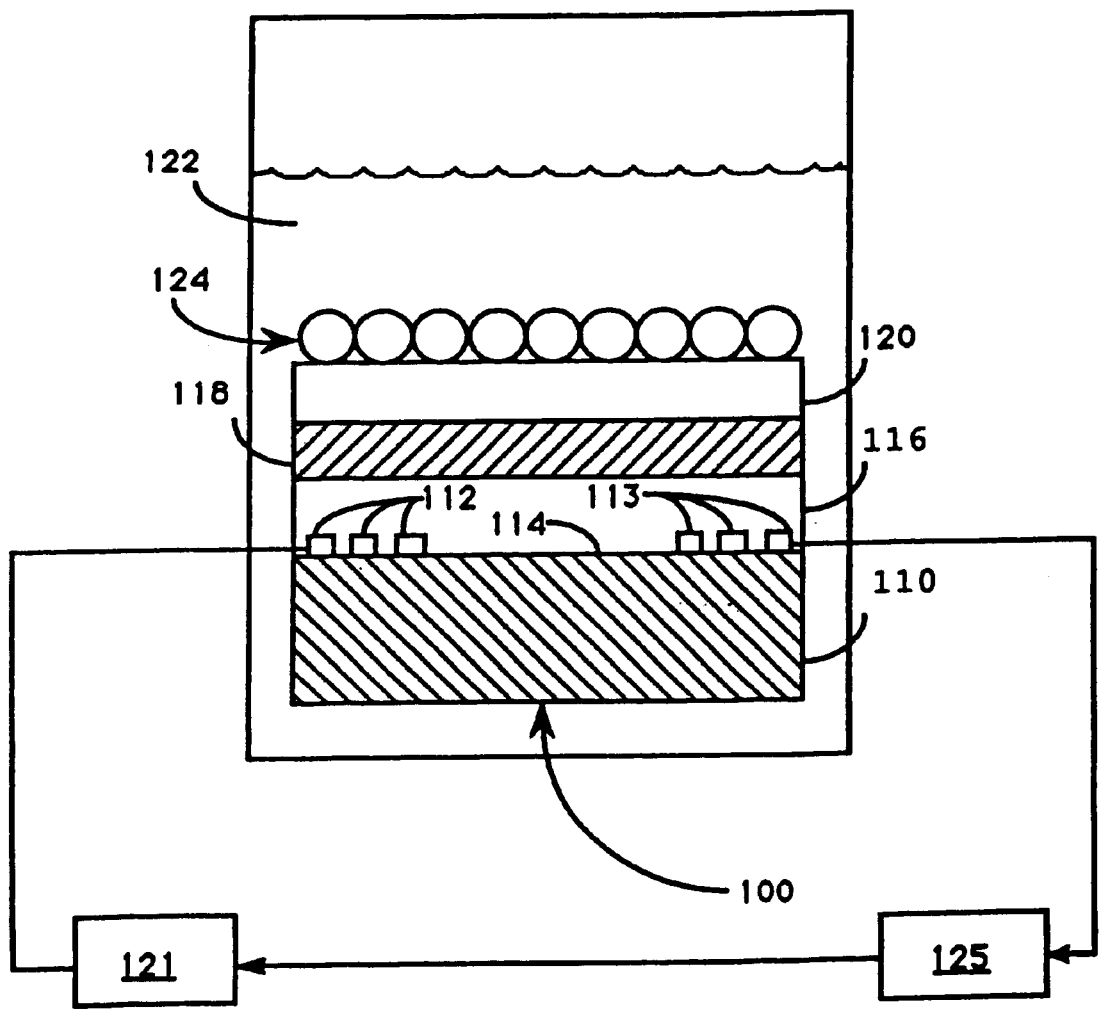
FIG. 1 is a schematic view of a sensor utilizing a surface transverse wave device with a chemically modified top surface.

In accordance with the present invention, a mass biosensor 100 comprises a surface transverse wave (STW) device 110 with input transducers 112 and output transducers 113 on its top surface 114, as shown in FIG. 1. A coupling layer 116, formed from an organosilane chemical, covers top surface 114. Coupling layer 116 serves as a site of attachment for an avidin layer 118, which binds tightly to a biotinylated antibody layer 120. Biotinylated antibody layer 120 can be replaced by other biotinylated compounds as appropriate for the particular application of the biosensor. A periodic signal produced by a signal generator 121 passes through the input transducers 112, where it is converted to a periodic acoustic wave and propagated along the surface transverse wave device 110, to the output transducers 113.

When the sensor is immersed in sample 122, antigen 124 binds to biotinylated antibody layer 120. The binding of antigen 124 causes the mass bound to surface 114 to change. This change is reflected in a change in propagation velocity of the acoustic wave between transducers 112 and 113. At the output transducers 113, the periodic acoustic wave is converted into a periodic electrical signal which passes to the signal processor 125. The signal indicating the frequency or relative phases is then used to calculate the amount of antigen 124 in sample 122.

After taking the measurement, antigen 124 can be stripped from biotinylated antibody layer 120 by washing with a high ionic strength salt solution such as 1.5 M NaCl. Different stripping methods are appropriate for use with other biotinylated conjugates. After the antigen is stripped from the antibody layer the biosensor can be reused.

Figure 2:
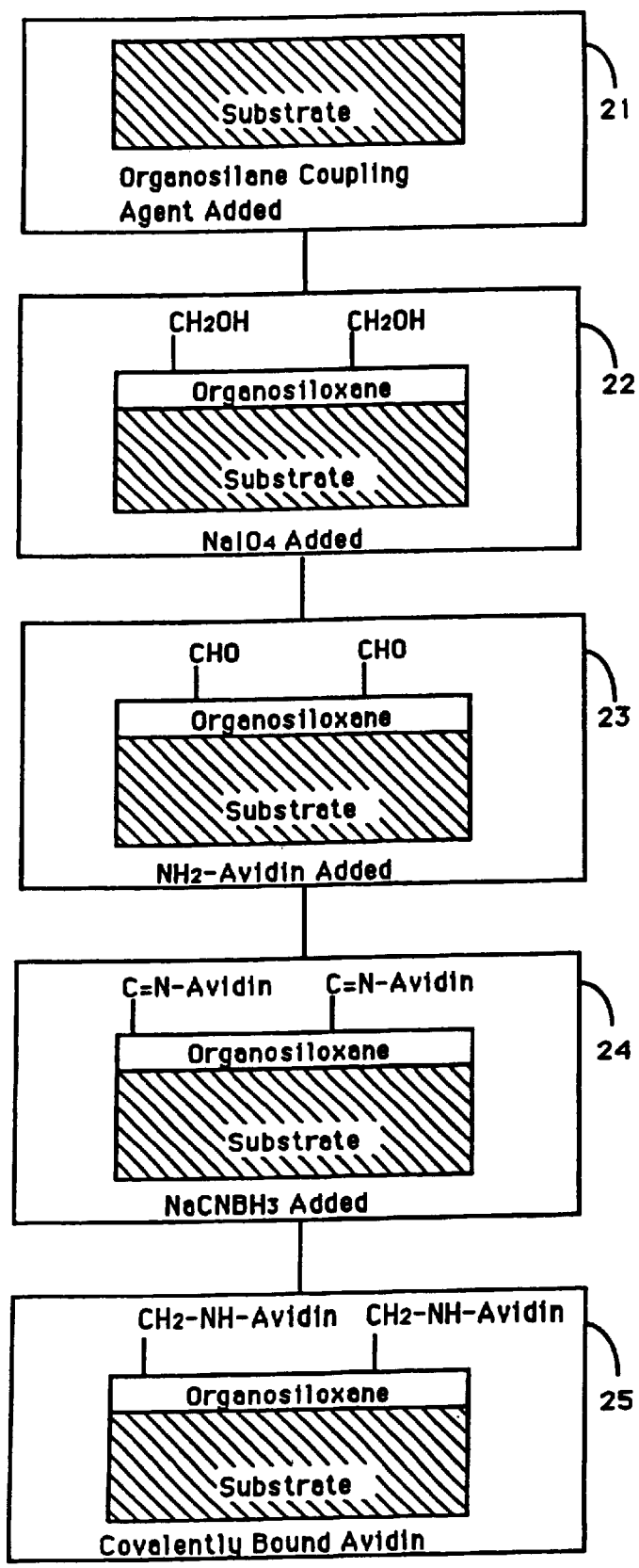
FIG. 2 is a schematic illustration of the process for immobilizing avidin to a substrate.

A schematic illustration of the process for immobilizing avidin to a quartz substrate is presented in FIG. 2. The substrate is pretreated by sputter deposition of $SiO_2$ to a thickness of 500 Angstroms to provide a number of active hydroxyl (—OH) groups. In the first step 21, an organosilane coupling agent is added to the substrate although other appropriate coupling agents could be used.

The organosilane coupling agent has a general formula of $R_nSiX_{(4-n)}$. X represents a hydrolyzable group, for example, alkoxy, acyloxy, amine, or chlorine. R represents a nonhydrolyzable organic radical containing a primary alcohol group. The integer n can be 1, 2, or 3 but is most typically 1. The R and X groups are bound to the central silicon atom (Si). The organosilane coupling agent is 3-glycidoxypropyltrimethoxysilane (GOPS). The chemistry for this step is as described in "Silane Coupling Agent Chemistry", Barry Arkles, *Petrarch Systems Register and Review*, R. Anderson, B. Arkles, and G. L. Larson, Eds., 1987. As a result, an organodihydroxysiloxane coats the substrate. In the second step 22, addition of a suitable oxidizing agent, such as sodium periodate, converts the primary alcohol groups on the organic radicals to reactive aldehydes. In the third step 23, avidin is added and the aldehydes react with a primary amine on avidin to form a labile Schiff's base. In the fourth step 24, a suitable reducing agent is added, such as sodium cyanoborohydride, which converts the labile complex to a stable reduction product represented in 25.

Streptavidin, a bacterial protein, can substitute for avidin since it has similar biotin binding properties. Avidin is a glycosylated protein, which means it has an abundance of sugar residues attached, providing potential sites for non-specific binding. Streptavidin is a nonglycosylated neutral protein which may be useful in certain applications for alleviating nonspecific binding. Modified forms of avidin or streptavidin, as, for example, by acetylation or succinylation, or genetically engineered avidin or streptavidin can also be used so long as the biotin binding sites remain intact.

Figure 3:
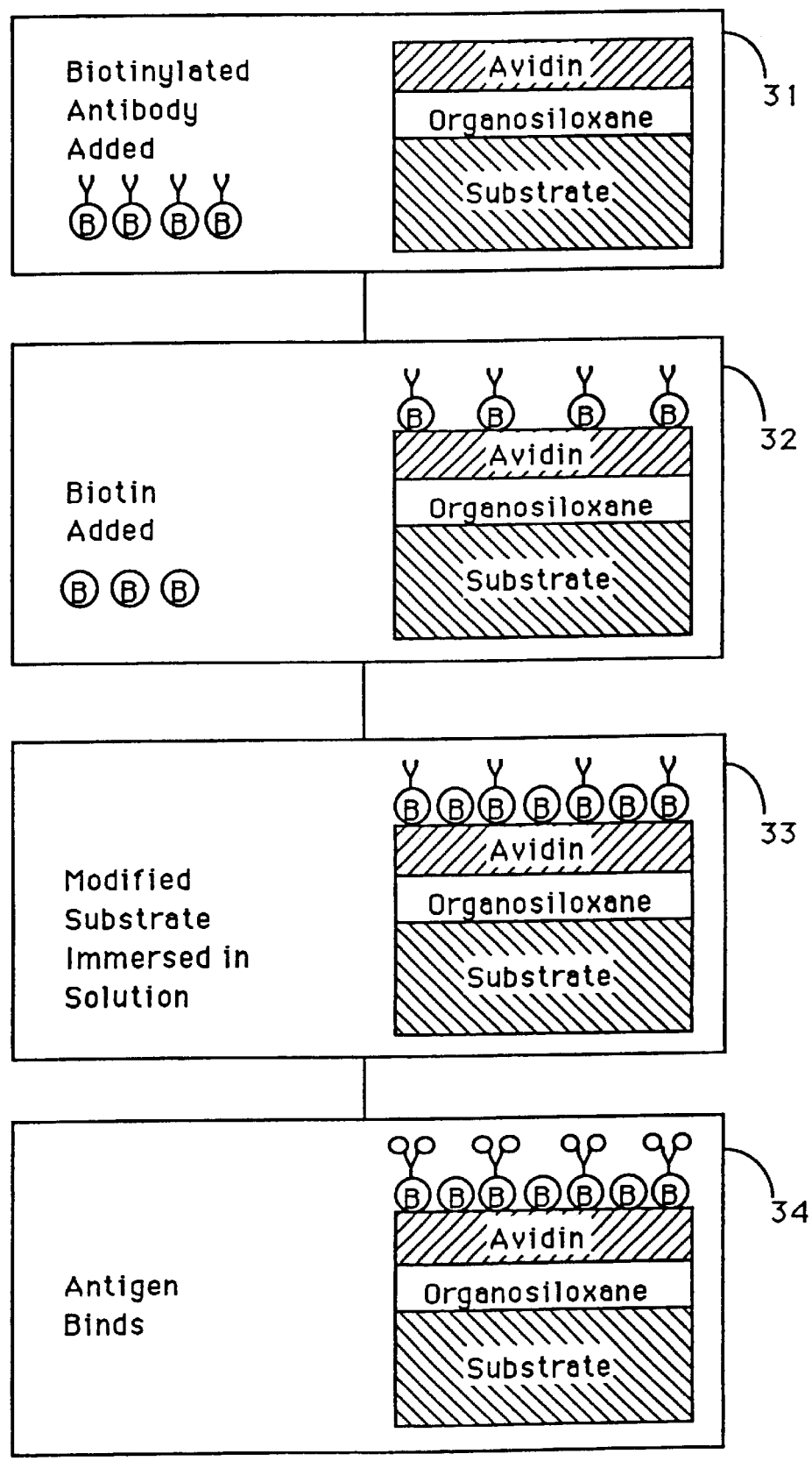
FIG. 3 is a schematic illustration of the process for attaching a biotinylated antibody to an avidin-coated substrate.

FIG. 3 is a schematic representation of the process for attaching a biotinylated antibody to the avidin-coated substrate in order to bind a particular antigen. The avidin-coated substrate is incubated with the biotinylated antibody in step 31. In step 32 the substrate is then washed with a blocking agent such as biotin which binds to any unoccupied sites on the avidin layer. Other blocking agents, such as glycine, can be used. When the substrate is immersed in sample solution in step 33, antigen binds to the surface via the antibody molecule, as shown in step, 34.

The immobilization process according to the invention is further explained hereinafter by reference to the following example.

EXAMPLE 1

Modification of a Silica Surface with Biotinylated Antibody

1. Silanization of Silica Substrate.

Prepare a 10% solution of 3-glycidoxypropyltrimethoxysilane (GOPS), pH 3.0, using 2.5 ml GOPS (Aldrich Chemical Co.), 20 ml isopropanol, 2.5 ml $H_2O$, and 1 ml acetic acid. Expose a silica substrate pretreated with $SiO_2$ to the solution. Allow the solution to hydrolyze 1 hour then add 0.25 ml triethylamine (Aldrich Chemical Co.), as catalyst. Allow 1 hour for binding. Rinse 3–5× with distilled water. Allow the surface to dry in vacuo or under helium, or in a mechanical oven at 110° C. for 10 minutes.

2. Oxidation of Epoxide or Diol Groups on GOPS by Periodate Oxidation.

Prepare a 0.1% periodate solution with 1 g. $H5IO_6$, 200 ml $H_2O$, 800 ml acetic acid. Incubate with the silanized substrate 30 minutes at room temperature. Wash with water.

3. Incubation of Substrate with Avidin.

Incubate the washed substrate with a solution of avidin in borate buffered saline (BBS), pH 8.5, at a concentration of 0.1 mg/ml. Mix by gentle inversion at 4° C. for 20–24 hours.

4. Reduction of Schiff's Base to a Stable Reduction Product.

Following the incubation, add $NaCNBH_4$ at three 15 minute intervals for a final concentration of 0.01M $NaCNBH_4$. Rinse with BBS.

5. Binding of Biotinylated Antibody.

Incubate avidin-layered substrate with biotin-conjugated antibody in PBS for 30 minutes at room temperature. Wash with PBS.

A surface layered with avidin can be customized by the user for widely different applications. Basically, the procedure utilizes a mixed conjugate comprising a biologically active molecule attached chemically to a ligand whereby the resultant product retains both its biological activity and its affinity for a ligand-binding protein. Any chemical pair that exhibits strong binding affinity toward one another is a candidate. For example, biotinylated antibodies bind antigens, biotinylated polynucleotide strands bind DNA, cDNA or RNA, biotinylated DNA-binding proteins bind regulatory sequences of genes, biotinylated Protein G and Protein A bind immunoglobulins, biotinylated lectins bind sugars, biotinylated enzymes bind their substrates, cofactors or inhibitors, and biotinylated cell receptor proteins bind hormones, neurotransmitters, or viruses. Any genetically engineered or chemically modified biotin can be substituted for biotin in the conjugate or as blocking agent as long as the avidin binding site remains available.

The method of the invention can be used on diverse substrates in accordance with the particular application. When purification is the objective, chromatographic support matrices, or silica beads can be used. Glass tubes, petri dishes, or other labware treated according to the method of the invention can be used to introduce time-saving steps and convenience to standard laboratory procedures.

Alternative methods of attachment of the avidin layer can be used. For example, an organosilane coupling agent whose nonhydrolyzable organic radical contains an amine group, (γ-aminopropyl)triethoxysilane (γ-APTES), can be reacted with glutaraldehyde and then with avidin. Some substrates, such as Sepharose, can be activated and attached directly to avidin.

The device of the invention accommodates any type of sensor, so that acoustical, optical, gravimetric, electrochemical, photoelectrochemical, capacitance, and thermistor sensors are all within the scope of the invention. Gravimetric sensors utilizing piezoelectric crystals include Rayleigh surface acoustic wave devices and Lamb acoustic wave devices as well as the surface transverse wave device. Fiber optic evanescent sensors and evanescent planar waveguide sensors are among the possible optical sensors. Among those in the electrochemical category, are potentiometric, amperometric and field-effect transistor (FET) sensors.

While avidin and biotinylated compounds are convenient binding substances to use because of their widespread availability, other reciprocal binding substances can be used according to the method of the invention. A lectin used as a first binding layer and a glycosylated receptor protein as its reciprocal binding layer will be applicable to the immobilization of virus particles, growth factors, hormones and other cell modulators. Alternatively, protein A or protein G can be incorporated in the first binding layer with antibody as the second binding layer so that the concentration of an antigen can be measured. These and other variations upon and modifications to the described embodiments are provided for by the present invention, the scope of which is limited only by the following claims.

What is claimed is:

1. A method for rendering a substrate surface specific for the binding of a selected substance, said method comprising the steps of:

Attaching to the surface of said substrate a layer of coupling agent which binds the layer to said substrate and which possesses binding sites for binding a ligand-binding substance thereto wherein said coupling agent is silyl compound of the formula:

$$R_nSiX_{(4-n)}$$

wherein R is a nonhydrolyzable organic radical containing a primary alcohol group, X is a hydrolyzable moiety selected from the group consisting of chloro, amino, alkoxy, and acyloxy, and n is an integer from 1 to 3;

attaching a layer of ligand-binding substance to said layer of coupling agent, said layer of ligand-binding substance having reciprocal binding sites available for binding said ligand-binding substance to said coupling agent as well as binding sites available for binding said ligand-binding substance to a ligand-bearing substance; and attaching a layer of ligand-bearing substance to said ligand-binding layer, said ligand-bearing substance having reciprocal binding sites available for binding said ligand-bearing substance to said ligand-binding substance as well as binding sites for binding of the selected substance; and washing the resulting structure with a blocking agent.

2. The method of claim 1 wherein said blocking agent is biotin.

3. The method of claim 1 wherein the ligand-binding substance is selected from the group consisting of avidin, streptavidin, genetically engineered avidin, genetically engineered streptavidin, modified avidin, and modified streptavidin; and said ligand-bearing substance is a biotinylated compound.

* * * * *